United States Patent
Nickisch et al.

(10) Patent No.: US 11,055,845 B2
(45) Date of Patent: Jul. 6, 2021

(54) VASCULAR TREE STANDARDIZATION FOR BIOPHYSICAL SIMULATION AND/OR AN EXTENSION SIMULATION FOR PRUNED PORTIONS

(71) Applicant: KONINKLIJKE PHILIPS N.V., Eindhoven (NL)

(72) Inventors: Hannes Nickisch, Hamburg (DE); Holger Schmitt, Luetjensee (DE); Sven Prevrhal, Hamburg (DE); Mordechay Pinchas Freiman, Zichron-Yaakov (IL); Liran Goshen, Pardes-Hanna (IL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 126 days.

(21) Appl. No.: 16/348,282

(22) PCT Filed: Nov. 16, 2017

(86) PCT No.: PCT/EP2017/079378
§ 371 (c)(1),
(2) Date: May 8, 2019

(87) PCT Pub. No.: WO2018/095791
PCT Pub. Date: May 31, 2018

(65) Prior Publication Data
US 2019/0318475 A1    Oct. 17, 2019

Related U.S. Application Data

(60) Provisional application No. 62/425,181, filed on Nov. 22, 2016.

(51) Int. Cl.
*G06T 7/00* (2017.01)
*G06T 7/162* (2017.01)
(Continued)

(52) U.S. Cl.
CPC ........... *G06T 7/0012* (2013.01); *A61B 6/032* (2013.01); *A61B 6/507* (2013.01); *A61B 6/5217* (2013.01);
(Continued)

(58) Field of Classification Search
None
See application file for complete search history.

(56) References Cited

U.S. PATENT DOCUMENTS 8,543,338 B2    9/2013    Bronstein
8,977,339 B1    3/2015    Wu
(Continued)

FOREIGN PATENT DOCUMENTS

| WO | 2011/093921 | 8/2011 |
| WO | 2014/072861 | 5/2014 |
| WO | 2016087396 | 6/2016 |

OTHER PUBLICATIONS

International Search Report and Written Opinion dated Mar. 7, 2018, for International Application No. PCT/EP2017/079378 filed Nov. 16, 2017.
(Continued)

*Primary Examiner* — Fayyaz Alam
(74) *Attorney, Agent, or Firm* — Larry Liberchuk

(57) ABSTRACT

A computing system (126) includes a computer readable storage medium (130) with computer executable instructions (128), including: a segmentation standardizer (120) configured to determine a standardized vascular tree from a segmented vascular tree segmented of volumetric image data and a predetermined set of pruning rules (206), and a biophysical simulator (122) configured to perform a biophysical simulation based on the standardized vascular tree. The computing system further includes a processor (124) configured to execute the segmentation standardizer to
(Continued)

determine the standardized vascular tree from the segmented vascular tree segmented of volumetric image data and the predetermined set of pruning rules, and configured to execute the biophysical simulator to perform a biophysical simulation based on the standardized vascular tree. The computing system further includes a display configured to display at least one of the standardized vascular tree and a result of the biophysical simulation.

27 Claims, 5 Drawing Sheets

(51) Int. Cl.
    *G06T 7/11*     (2017.01)
    *G16H 30/40*     (2018.01)
    *A61B 6/03*     (2006.01)
    *A61B 6/00*     (2006.01)
    *G16H 50/50*     (2018.01)

(52) U.S. Cl.
    CPC ................ G06T 7/11 (2017.01); G06T 7/162 (2017.01); G16H 30/40 (2018.01); *G06T 2207/10072* (2013.01); *G06T 2207/30101* (2013.01); *G16H 50/50* (2018.01)

(56) References Cited

U.S. PATENT DOCUMENTS

| | | | |
|---|---|---|---|
| 9,042,611 B2 | 5/2015 | Blezek | |
| 9,087,147 B1 | 7/2015 | Fonte | |
| 9,424,395 B2 | 8/2016 | Sankaran | |
| 2004/0002660 A1 | 1/2004 | Mielekamp | |
| 2013/0202170 A1* | 8/2013 | Blezek | G16H 30/40 382/131 |
| 2015/0032435 A1 | 1/2015 | Yagi | |
| 2015/0282765 A1* | 10/2015 | Goshen | A61B 5/0263 600/408 |
| 2016/0206265 A1 | 7/2016 | Schmitt | |
| 2016/0296287 A1 | 10/2016 | Taylor | |
| 2020/0359985 A1* | 11/2020 | Carmi | G06T 7/0012 |

OTHER PUBLICATIONS

Nickisch et al: "Learning Patient-Specific Lumped Models for Interactive Coronary Blood Flow Simulations", Nov. 20, 2015, Springer International Publishing.

* cited by examiner

VASCULAR TREE STANDARDIZATION FOR BIOPHYSICAL SIMULATION AND/OR AN EXTENSION SIMULATION FOR PRUNED PORTIONS

CROSS REFERENCE TO RELATED APPLICATIONS

This application is the U.S. National Phase application under 35 U.S.C. § 371 of International Application No. PCT/EP2017/079378 filed Nov. 16, 2017, published as WO 2018/095791 on May 31, 2018, which claims the benefit of U.S. Provisional Patent Application No. 62/425,181 filed Nov. 22, 2016. These applications are hereby incorporated by reference herein.

FIELD OF THE INVENTION

The following generally relates to biophysical simulation such as Fractional Flow Reserve (FFR), instantaneous wave-free ratio (iFR), flow simulations and/or other biophysical simulation and more particularly to a vascular tree standardization for biophysical simulation and/or an extension to the biophysical simulation for portions of vessels pruned off the vascular tree during the standardization, and is described with particular application to Fractional Flow Reserve-computed tomography (FFR-CT). However, the following is also amenable to other imaging modalities including X-ray, magnetic resonance imaging (MRI), and/or other imaging modalities, and/or other biophysical simulations.

BACKGROUND OF THE INVENTION

Coronary artery disease is among the single largest cause of death worldwide. Fractional Flow Reserve (FFR) is an established invasive measure in the catheterization laboratory (Cath Lab) to quantify, via an FFR index, the hemodynamic significance of a coronary lesion due to calcified or soft plaque. The index indicates the functional severity of a coronary stenosis that is calculated from pressure measurements made during coronary arteriography and is defined as the distal blood pressure (behind a stenosis) relative to the proximal pressure (close to the ostium) under hyperemic conditions. That is, the FFR index expresses the maximal flow down a vessel in the presence of a stenosis compared to the maximal flow in the hypothetical absence of the stenosis. The FFR value is an absolute number between 0 and 1, where a value 0.50 indicates that a given stenosis causes a 50% drop in blood pressure.

FFR is an invasive procedure in that it requires insertion of a catheter into the femoral or radial arteries and advancement of the catheter to the stenosis where a sensor at the tip of the catheter senses pressure, temperature, and flow across the stenosis, during conditions promoted by various agents that effect vessel geometry, compliance and resistance, and/ or other characteristics. FFR-CT is a non-invasive simulation-based surrogate for invasive FFR based on a standard cardiac CT angiogram (CCTA). This approach estimates the FFR index is through computational fluid dynamic (CFD) simulations in which blood flow and pressure through the coronaries is simulated. One simulation approach, unfortunately, requires the CCTA be sent to an off-site central data center for processing, including cardiac segmentation, coronary segmentation and FFR simulation, which can delay results.

The length of automatically segmented coronary arteries in a conventional CTA scan depends on the effective image resolution and a good contrast agent uptake in the coronaries. Furthermore, in semi-automatic segmentation with a human operator guiding the coronary tree extraction, the ability and effort of the human operator are also strongly contributing to the number and length of the extracted vessels. Boundary conditions of patient-specific biophysical models used in FFR-CT predictions are supposed to simulate the effect of the microvasculature which is typically invisible in the image. They are usually applied at the distal ends of the coronary segmentation. Population averages and/or scaling laws are used to shape the boundary conditions; hence they depend on the local size and width of the vessel and, as a consequence, also on the operator, the image resolution etc. Unfortunately, this can hamper the reproducibility and reliability of FFR-CT simulations.

SUMMARY OF THE INVENTION

Aspects described herein address the above-referenced problems and others.

In one aspect, a computing system includes a computer readable storage medium with computer executable instructions including: a segmentation standardizer configured to determine a standardized vascular tree from a segmented vascular tree segmented of volumetric image data and a predetermined set of pruning rules, and a biophysical simulator configured to perform a biophysical simulation based on the standardized vascular tree. The computing system further includes a processor configured to execute the segmentation standardizer to determine the standardized vascular tree from the segmented vascular tree segmented of volumetric image data and the predetermined set of pruning rules, and configured to execute the biophysical simulator to perform a biophysical simulation based on the standardized vascular tree. The computing system further includes a display configured to display at least one of the standardized vascular tree and a result of the biophysical simulation.

In another aspect, a computer readable storage medium is encoded with computer readable instructions, which, when executed by a computer processor of a computing system, causes the computer processor to: execute a segmentation standardizer configured to determine a standardized vascular tree from a segmented vascular tree segmented of volumetric image data using a predetermined set of pruning rules, execute a biophysical simulator configured to perform a biophysical simulation based on the standardized vascular tree, and display via a display monitor configured to display at least one of the standardized vascular tree and a result of the biophysical simulation.

In another aspect, a method includes standardizing a segmented vascular tree using a predetermined set of pruning rules, thereby creating a standardized vascular tree. The method further includes performing a biophysical simulation for the standardized vascular tree. The method further includes displaying a result of the biophysical simulation.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

The following generally relates to vascular tree standardization for a biophysical simulation and/or an extension to the biophysical simulation for portions of vessels pruned off the vascular tree during the standardization. For sake of brevity and explanatory purposes, the following is described with particular application to a non-limiting example of FFR-CT. However, it is to be understood the standardized vascular tree can be used with an application that uses a vacular or other tree structure.

Figure 1:
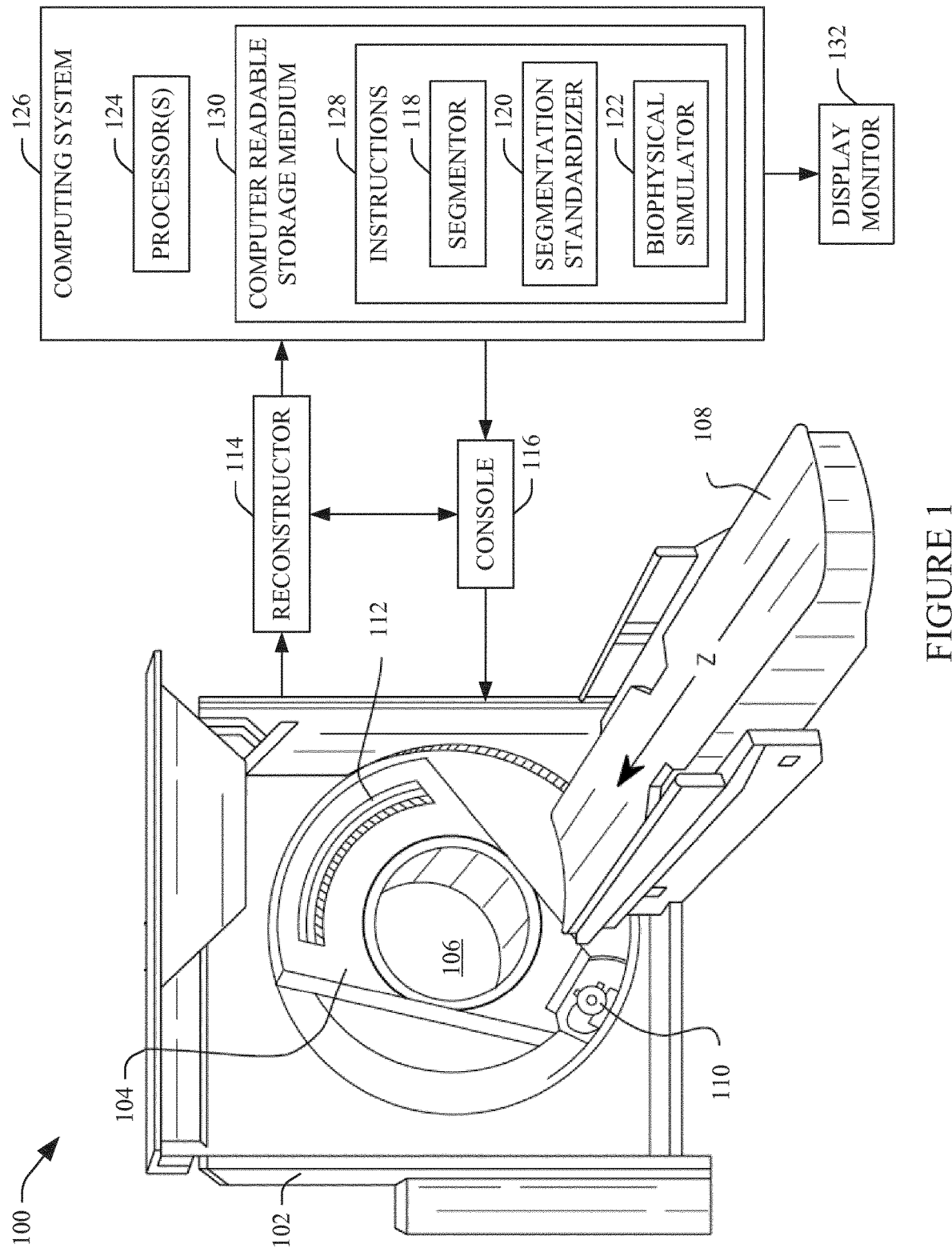
FIG. 1 schematically illustrates a computing system, which is configured at least to standardize a segmented vascular tree by selectively pruning off portions thereof and determine an FFR index for the standardized vascular tree and, optionally, selectively pruned off portions.

FIG. 1 schematically illustrates an imaging system 100 such as a CT scanner. The imaging system 100 includes a generally stationary gantry 102 and a rotating gantry 104, which is rotatably supported by the stationary gantry 102 and rotates around an examination region 106 about a z-axis. A subject support 108, such as a couch, supports an object or subject in the examination region 106.

A radiation source 110, such as an x-ray tube, is rotatably supported by the rotating gantry 104, rotates with the rotating gantry 104, and emits radiation that traverses the examination region 106. A radiation sensitive detector array 112 subtends an angular arc opposite the radiation source 110 across the examination region 106. The radiation sensitive detector array 112 detects radiation traversing the examination region 106 and generates a signal indicative thereof for each detected photon.

A reconstructor 114 reconstructs the projection data, generating volumetric image data indicative of a scanned portion of a subject or object located in the examination region 106. A general-purpose computing system or computer serves as an operator console 116. The console 116 includes a human readable output device such as a monitor and an input device such as a keyboard, mouse, etc. Software resident on the console 116 allows the operator to interact with and/or operate the scanner 100 via a graphical user interface (GUI) or otherwise.

A segmentor 118 is configured to facilitate segmenting a vascular tree from the volumetric image data. In one instance, this includes segmenting the coronary tree, identifying center lines of the vessels of the segmented coronary tree, labeling main vessels such as the left coronary artery (LCA), the right coronary artery (RCA), the left anterior descending artery (LDA), etc., and/or labeling a location(s) of interest such as a location of a stenosis. Manual, semi-automatic and/or automatic segmentation approaches can be utilized. Examples of segmentations are described in Billow et al., "A General Framework for Tree Segmentation and Reconstruction from Medical Volume Data," MICCAI 2004, Vol. 3216, Lecture Notes in Computer Science, pp 533-540, and Giilsiin et al., "Coronary Centerline Extraction via Optimal Flow Paths and CNN Path Pruning," MICCAI 2016, Vol. 9902, Lecture Notes in Computer Science, pp 317-325.

A segmentation standardizer 120 is configured to standardize the segmented vascular tree. As described in greater detail below, in one non-limiting instance this includes applying a set of predetermined rules, which selectively prunes or modifies one or more vessels of the vascular tree, including taking into consideration locations of interest, to a "standardized" configuration or tree. As such, a shape, a size and/or geometry of the vascular tree used to determine an FFR (the standardized vascular tree) depends only little, if any, on image resolution, contrast uptake, and/or the operator's segmentation, unlike the original segmentation. Subsequent FFR-CT simulations will be reliable with faithful boundary conditions and accurate predictions.

A biophysical simulator 122 is configured to at least process the standardized segmented vascular tree to perform a biophysical simulation. With respect to FFR, the biophysical simulator determines an FFR index therefor. As described in greater detail below, in a variation, the simulation is extended to the pruned regions using results of the simulation with the standardized segmented vascular tree for determining initial conditions for the pruned portions. As such, the approach described herein enforces boundary conditions in simulations not just at the inlets and outlets but at locations inside the vessels of the vascular tree. As a result, standardized patient-specific biophysical simulations can be performed where the standardization is achieved through shifting the boundary conditions and extending the simulation beyond.

Examples of FFR approaches are described in patent application serial number U.S. Ser. No. 14/396,407, publication US 2015/0092999 A1, filed May 10, 2013, and entitled "Determination of a fractional flow reserve (ffr) value for a stenosis of a vessel," patent application serial number U.S. Ser. No. 14/437,990, publication US 2015/0282765 A1, filed Oct. 24, 2013, and entitled "Fractional flow reserve (ffr) index," and patent application serial number U.S. Ser. No. 14/059,517, publication US 2015/0112191 A1, filed Oct. 22, 2013, and entitled "Fractional flow reserve (ffr) index with adaptive boundary condition parameters," all three of which are incorporated herein by reference in their entireties. The FFR index can be displayed via a display monitor 132, stored, conveyed to another device, etc.

In the illustrated example, the segmentor 118, the segmentation standardizer 120 and/or the biophysical simulator 122 is implemented with one or more computer processors 124 (e.g., a central processing unit or CPU, a microprocessor, etc.), of a computing system 126, that execute one or more computer readable instructions 128 stored in one or more computer readable storage mediums 130 (which excludes transitory medium) such as physical memory and/or other non-transitory storage medium. The processor(s) 124 may additionally or alternatively execute one or more computer readable instructions carried by a carrier wave, a signal and/or other transitory medium. The instructions 128 are executed onsite, as shown. In another instance, one or more of the instructions 128 is computed remote from the systems 126, e.g., via a "cloud" and/or other computing resource or service.

Figure 2:
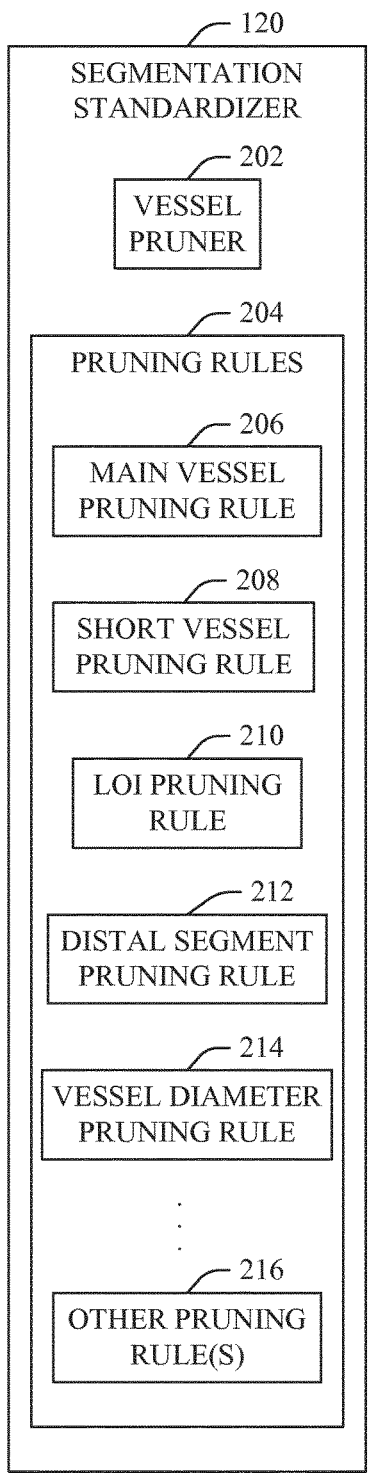
FIG. 2 schematically illustrates an example of a segmentation standardizer used to standardize the segmented vascular tree.

FIG. 2 schematically illustrates an example of the segmentation standardizer 120.

The illustrated example of the segmentation standardizer 120 includes a vessel pruner 202 configured to prune the segmented vascular tree using a predetermined set of pruning rules 204. The predetermined set of pruning rules 204 includes N rules, where N is a positive integer. In one instance, the predetermined set of pruning rules 204 is a default set of rules. In another instance, the predetermined set of pruning rules 204 includes at least one user and/or facility defined rule. In another instance, the predetermined set of pruning rules 204 includes a combination of default and user and/or facility defined rules.

The illustrated predetermined set of pruning rules 204 includes a main vessel pruning rule 206, a short vessel pruning rule 208, a location of interest (LOI) pruning rule 210, a distal segment pruning rule 212, a vessel diameter pruning rule 214 and/or one or more other pruning rule 216. In a variation, the one or more other pruning rule 216 is omitted, and the predetermined set of pruning rules 204 includes only the rules 206-214. In another embodiment, one or more of the rules 206-214 is omitted. Another pruning rule can be based on a patient specific parameter, which can be specific to the resolution of the image data, patient anatomy, and/or demographics such as male or female, adult or child, etc.

An example of the main vessel pruning rule 206 is a main vessel (e.g., RCA, LCA, LAD, etc.) is pruned only if its length, e.g., from the ostium of the aorta along the centerline, is greater than a predetermined length. If a main vessel length is equal to or less than the predetermined length, the main vessel is not pruned. If a main vessel length is greater than the predetermined length, the main vessel is pruned, but only to the predetermined length. In one instance, the predetermined length is a single value in a range of eight centimeters (8 cm) to twelve centimeters (12 cm). In another instance, the predetermined length is a single value in a range of nine centimeters (9 cm) to eleven centimeters (11 cm). In another instance, the predetermined length is ten centimeters (10 cm).

An example of the short vessel pruning rule 210 is a vessel is pruned off if it has a length that is less than a predetermined length along the centerline. Hence, if a vessel has a length that is less than the predetermined length, the vessel is removed from the vascular tree. If the vessel has a length that is equal to or greater than a predetermined length, the vessel is not pruned. In one instance, the predetermined length is in a range of a quarter to two centimeters (0.25-2.0 cm). In another instance, the predetermined length is in a range of a half to one and a half centimeters (0.5-1.5 cm). In another instance, the predetermined length is one centimeter (1 cm).

An example of the location of interest pruning rule 210 is an end of a vessel is pruned only if its length from an identified location of interest, which can be identified via a mouse click on a displayed portion of a vessel and/or otherwise, it is greater than a predetermined length. If the length is equal to or less than the predetermined length from the location of interest the end is not pruned. If the length is greater than the predetermined length the end is pruned but only to the predetermined length. In one instance, the predetermined length is in a range of a half to three centimeters (0.5-3.0 cm). In another instance, the predetermined length is in a range of one to two and a half centimeters (1.0-2.5 cm). In another instance, the predetermined length is two centimeters (2.0 cm).

An example of the distal segment pruning rule 212 is a most distal segment, which is a segment behind a most distal branch, is pruned if its length is greater than a predetermined length from a bifurcation. If the length of the most distal segment is equal to or less than the predetermined length, the most distal segment is not pruned. If the length of the most distal segment is greater than the predetermined length, the most distal segment is pruned but only to the predetermined length. In one instance, the predetermined length is in a range of a half to three centimeters (0.5-3.0 cm). In another instance, the predetermined length is in a range of one to two and a half centimeters (1.0-2.5 cm). In another instance, the predetermined length is two centimeters (2.0 cm).

In one instance, the example distal segment pruning rule 212 is constrained by the main vessel pruning rule 206 and the location of interest pruning rule 210. For example, the distal segment pruning rule 212 is applied only if the result satisfies the main vessel pruning rule 206 and the location of interest pruning rule 210. If the result of the distal segment pruning rule 212 would not satisfy the main vessel pruning rule 206 and the location of interest pruning rule 210, the distal segment pruning rule 212 is not applied. For example, is applying the distal segment pruning rule 212 would result in a main vessel less than 10 cm or a distal end from a location of interest less than 2 cm, the rule 212 is not applied.

An example of the vessel diameter pruning rule 212 is a vessel is pruned from an outlet (the vessel end) towards an inlet (the region where it is connected to another vessel or the aorta) if a diameter of the vessel is greater than a predetermined vessel diameter. If a vessel diameter is equal or less than the predetermined diameter, the vessel is not pruned. If the vessel diameter is greater than the predetermined diameter, the vessel is pruned but only until the vessel diameter is equal to or less than the predetermined diameter. In one instance, the predetermined diameter is in a range of a half to two and a half millimeters (0.5-2.5 mm). In another instance, the predetermined diameter is in a range of one to two millimeters (1.0-2.0 mm). In another instance, the predetermined diameter is one and a half millimeters (1.5 mm).

By applying the pruning rules described herein, the standardized vascular tree, which is the tree used to compute the FFR index, at least fulfils one or more of: 1) vessel segments have a standardized length after the last branching location; 2) the distal part of the vessels with too small diameter that is not well-defined under a fixed image resolution have little relevance; 3) vessel stumps i.e. very short vessels have unreliable size/volume are ignored; 4) major vessels such as LAD, LCA and RCA have a minimum length; and 5) possible locations of interest to a human operator such as stenoses and/or locations of the vascular tree. The rules do not alter the centerline or the lumen segmentation; they merely define the support of the simulation, the location where the boundary conditions are applied, and the anatomical parameters of the boundary condition model.

Standardization parameters can be fixed for all population and chosen from some range by an optimization process over entire training population. Alternatively, the standardization parameters can be personalized from the range for each patient by using patient properties including but not limited to demographic and/or anatomical patient properties such as patient sex, weight, age, heart size.

With one FFR-CT approach, the pruning rules 206 optimize FFR-CT predictions of a lumped model pipeline such that they are as accurate as possible. For example, the pruning rules 206 optimize the FFR-CT predictions of a lumped model pipeline of Nickisch et al., "Learning Patient-Specific Lumped Models for Interactive Coronary Blood Flow Simulations," MICCAI 2015, pp. 433-441. The pruning rules 206 may also optimize other FFR-CT predictions of a lumped model pipeline. Empirically, the pruning rules 204 decrease user dependence of the simulation and increase the accuracy of lumped model pipeline. Other simulations, including other FFR-CT, not using a lumped model are also contemplated herein. For example, simulations based on a mesh such as Finite Elements, Finite Volume, Finite Differences, as well as mesh-free approaches such as particle methods or lattice Boltzman, and/or other approaches are contemplated herein.

Figure 3:
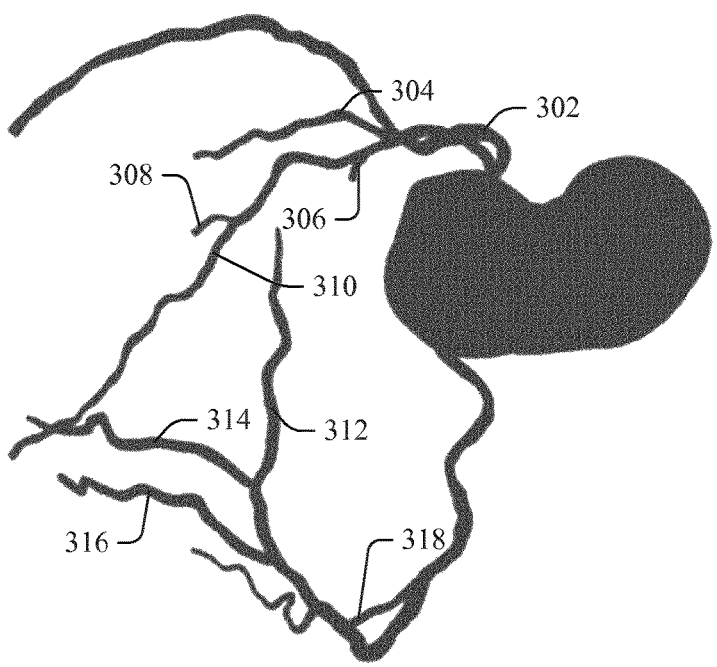
FIG. 3 shows an example of a segmented vascular tree before pruning by the segmentation standardizer.
Figure 4:
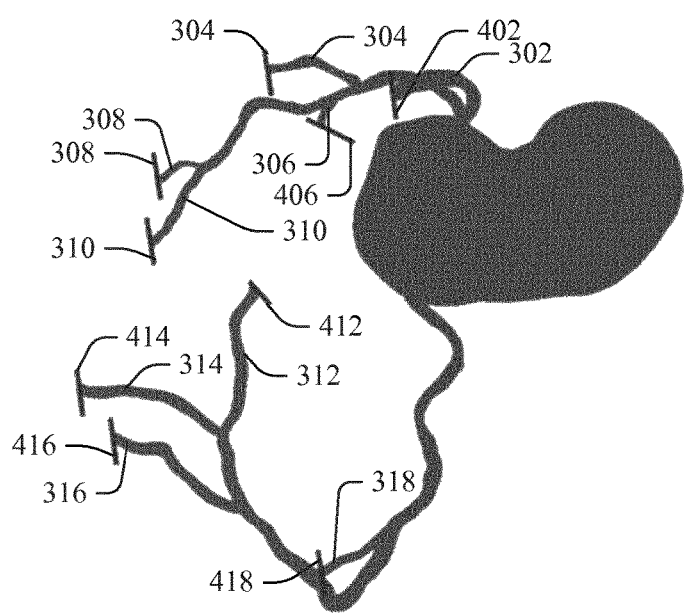
FIG. 4 shows an example of the segmented vascular tree of FIG. 3 after pruning by the segmentation standardizer using the pruning rules described herein.

FIG. 3 shows a segmented coronary tree, e.g., output by the segmentor 118. FIG. 4 shows a standardized segmented coronary tree, after the segmentation standardizer 120 applies the pruning rules 204 to the segmented coronary tree of FIG. 3. In this example, the rules resulted in pruning ends of vessels 302, 304 306, 308, 310, 312, 314, 316, and 318. FIG. 4 shows pruning markers 402, 404 406, 408, 410, 412, 414, 416, and 418 located at points along the vessels 302, 304 306, 308, 310, 312, 314, 316, and 318 at which ends were pruned. In a variation, the pruned portions could be grayed out and/or otherwise marked.

Figure 5:
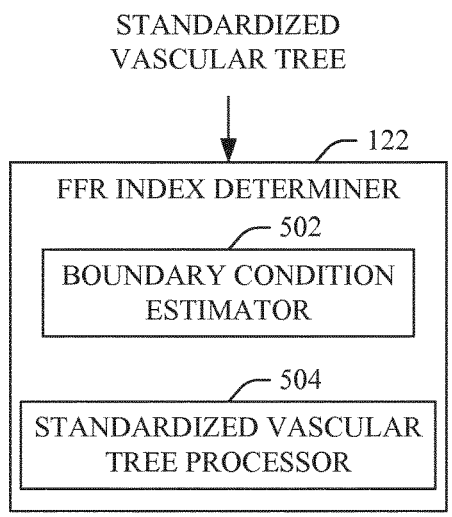
FIG. 5 schematically illustrates an example of a FFR index determiner that computes an FFR index for the standardized vascular tree.

FIG. 5 schematically illustrates an example in which the biophysical simulator 122 is an FFR index determiner. The FFR index determiner 122 receives the standardized vascular tree (e.g., FIG. 4) as an input.

The FFR index determiner 122 includes a boundary condition estimator 502, which is configured to estimate one or more boundary conditions for the standardized vascular tree. For example, the boundary condition estimator 502 may determine and/or receive an inlet flow-rate $Q_o$ (i.e., a flow rate at the ostium), which can be generated based on data such as subject weight, body mass index (BMI), gender, age, blood test results, anatomical imaging data (e.g., myocardium mass and estimated stroke-volume), and/or subject data, and a geometry of the standardized vascular tree (e.g., a diameter at the ostium $D_o$). From this, the boundary condition estimator 502 estimates at least one boundary condition such as flow rate Q, average velocity, and/or resistance, at the vessel outlets.

By way of non-limiting example, in one instance the boundary condition estimator 502 estimates a flow rate boundary condition Q at the outlet as a function of $Q_o$ and $D_o$ as $$Q = Q_o \left(\frac{D}{D_o}\right)^{\frac{7}{3}}$$

where D is the effective diameter at each outlet, an average velocity as $$v = \frac{\pi}{4} K D^{\frac{1}{3}}$$

where K is a ratio of vessel length to diameter, and a resistance boundary condition as $$R \stackrel{def}{=} \frac{P}{Q}$$

where, for healthy vessels, $P_o \cong P$, where $P_o$ is the aortic pressure at the ostium, which can be determined by measuring the brachial blood pressure, and the resistance of healthy tissue $R_h$ can be determined as $$R_h \cong \frac{P_o}{Q_o \left(\frac{D}{D_o}\right)^{\frac{7}{3}}}.$$

The FFR index determiner 122 further includes a standardized vascular tree processor 504, which performs a computational fluid dynamic (CFD) simulation on the standardized vascular tree using the boundary conditions and determines an FFR based on the CFD results. The output of the CFD includes volumetric information of pressure and velocity, and the FFR is computed based thereon. For example, the FFR is computed as a ratio of maximum blood flow distal to a stenotic lesion (Pd) to normal maximum flow in the same vessel (Pa), or FFR=Pd/Pa. Another suitable approach is described in Nickisch et al., "Learning Patient-Specific Lumped Models for Interactive Coronary Blood Flow Simulations," MICCAI 2015, Part II, LNCS 9350, pp. 433-441, 2015.

Figure 6:
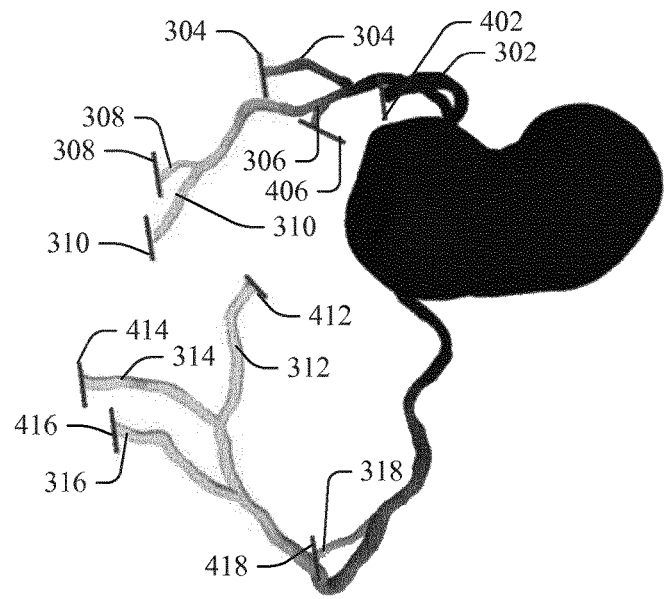
FIG. 6 shows the standardized vascular tree with the FFR index superimposed there over.

FIG. 6 shows an example displayed output showing the standardized vascular tree (FIG. 5) with the simulation results (e.g., in gray scale) superimposed or overlaid over the vessels 302, 304 306, 308, 310, 312, 314, 316, and 318. In this example, the pruning markers 402, 404 406, 408, 410, 412, 414, 416, and 418 are shown to show the point at which the vessels 302, 304 306, 308, 310, 312, 314, 316, and 318 were pruned. This allows the user to see where any pruning was performed. In a variation, the pruning markers are not displayed. In FIG. 6, there are no simulation results for the pruned off portions of the vessels (i.e. portions distal to pruning makers 402-418), which are not displayed.

Figure 7:
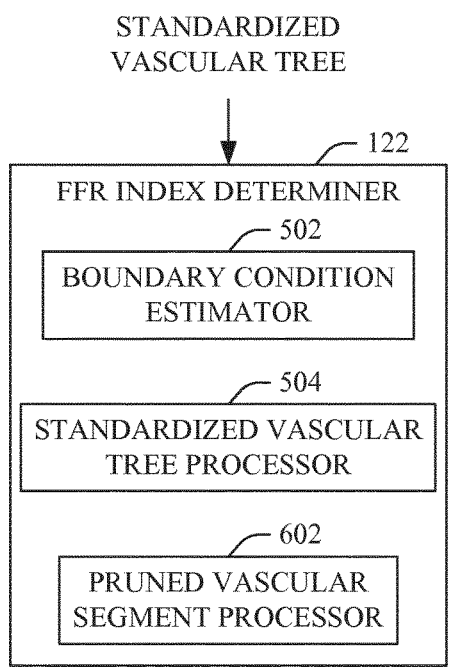
FIG. 7 schematically illustrates an example of a FFR index determiner that computes an FFR index for the standardized vascular tree and the pruned portions.

FIG. 7 is substantially similar to FIG. 5 except that the FFR index determiner 122 further includes a pruned vascular segment processor 602. The pruned vascular segment processor 602 is configured to determine an FFR value for pruned portions of the vessels using boundary conditions based on the output of the standardized vascular tree processor 504. The pruned vascular segment processor 602 extends flow simulations beyond the initial simulation domain of the standardized vascular tree (e.g., FIG. 4). In one instance, the pruned vascular segment processor 602 utilizes a lumped parameter model, as s described below. However, as described herein, other approaches such as mesh, mesh-free, etc. are also contemplated herein.

Figure 9:
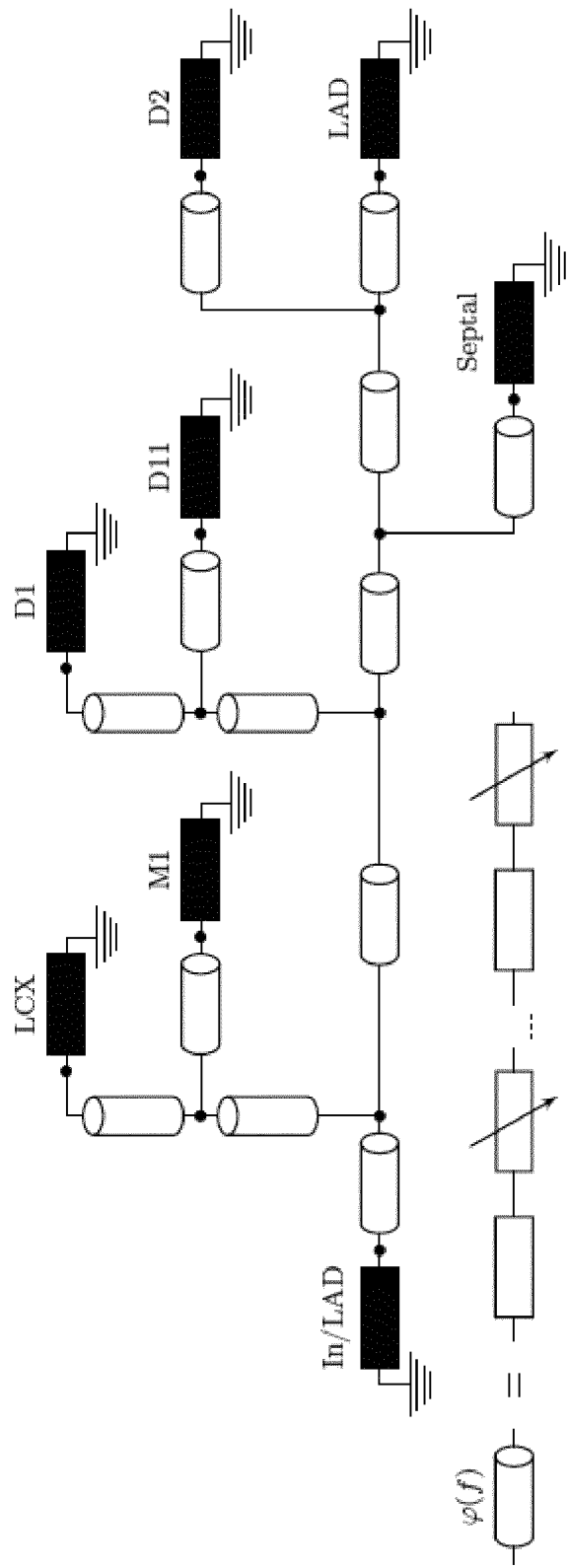
FIG. 9 schematically illustrates a lumped parameter model for modelling the pruned portions.

An example of a suitable lumped parameter model is shown in FIG. 9. This example includes n elements and m nodes including ground, where n and m are positive integers. Based on the centerline representation, a lumped model is set up with nonlinear resistances. The black boxes indicate inflow and outflow boundary conditions. The white tubes representing tree segment transfer functions $\phi(f)$ are composed of a series of linear and nonlinear resistance elements reflecting both the local vessel geometry and hydraulic effects. From this, the pruned vascular segment processor 602 considers the pruned portions of the vessels as sequences of non-linear hydraulic resistance elements.

For a continuation of a pruned vessel, a volumetric flow rate and an absolute pressure of the pruned simulation at the pruning location (the pruning markers 402-418) are retrieved or read. These values are used as initial values for a subsequent simulation comprising just the pruned part distal the pruning location. For a vessel without branching points, the flow is constant across the vessel. The simulation is an evaluation of the local transfer functions along the pruned vessel.

Where an entire subtree is pruned away, an entire hydraulic network (with corresponding inlet conditions) is simulated. In one instance, this includes solving a system of nonlinear equations to obtain the respective flows and pressures. An example a system of nonlinear equations is:

$$\begin{bmatrix} A_R R^{-1} A_R^T & A_P \\ A_P^T & 0 \end{bmatrix} \begin{bmatrix} q \\ f_P \end{bmatrix} = \begin{bmatrix} -A_F \hat{f}_F \\ \hat{P}_P \end{bmatrix} + \begin{bmatrix} -A_V \varphi^{-1}(A_V^T q) \\ 0 \end{bmatrix}$$

where A represents a node-to-element matrix, the subscripts R, P, F and V respectfully indicate resistor, pressure source, flow source and varistor, R is a diagonal resistance matrix, $\hat{f}_F$ and $\hat{P}_P$ are vectors containing pressure/flow source parameters, $\varphi^{-1}$ is an inverse varistor transfer functions stacked into a vector, q contains absolute pressures relative to a ground node, and $f_P$ represents the volumetric flow rate at pressure sources. A suitable set of outlet boundary conditions include resistances or outlet flows using a population scaling law.

Where a subtree or a vessel is entirely removed in the pruning process and the subtree or vessel was branching from another vessel, then there is no flow left and a value of zero is assigned, and, thus, constant pressure and constant FFR values are assigned along the entire subtree. Everything beyond that would require a way of determining which part of the main flow would be going through the subtree or vessel and would finally require a modification of the simulation results on the pruned domain.

Figure 8:
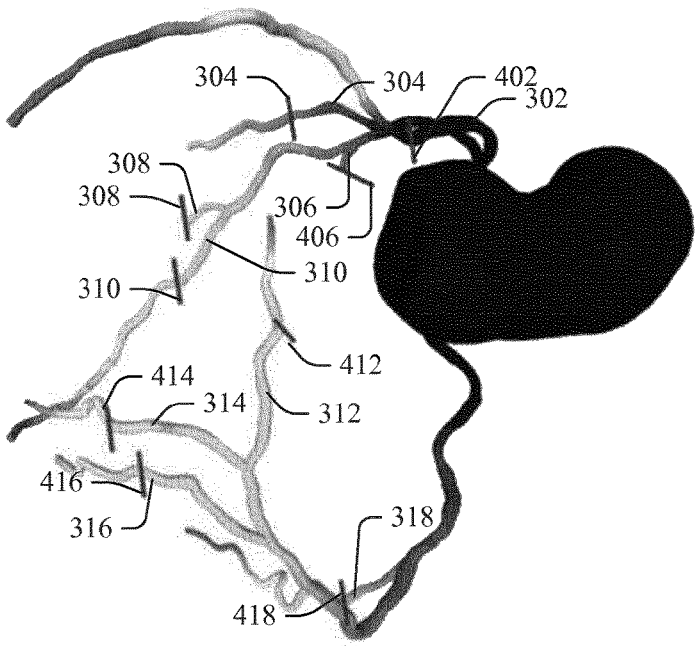
FIG. 8 shows the segmented vascular tree with the FFR index for the standardized vascular tree and the pruned portions superimposed there over.

FIG. 8 shows an example displayed output showing the standardized vascular tree (FIG. 6) with the pruned portions and simulation results, therefore (in gray scale) are superimposed or overlaid over the vessels 302, 304 306, 308, 310, 312, 314, 316, and 318. In this example, the pruning markers 402, 404 406, 408, 410, 412, 414, 416, and 418 are again shown to show the point at which the vessels 302, 304 306, 308, 310, 312, 314, 316, and 318 were pruned. In a variation, the pruning markers are not displayed.

The approach described herein allows for performing standardized patient-specific biophysical simulations where the standardization is not constrained to the hard pruning of the segmentation standardizer 120. For example, the result of the computation on the reduced domain is used as a starting point, and then the results for the separate parts of the entire domain are subsequently added without modifying the results on the reduced domain.

Figure 10:
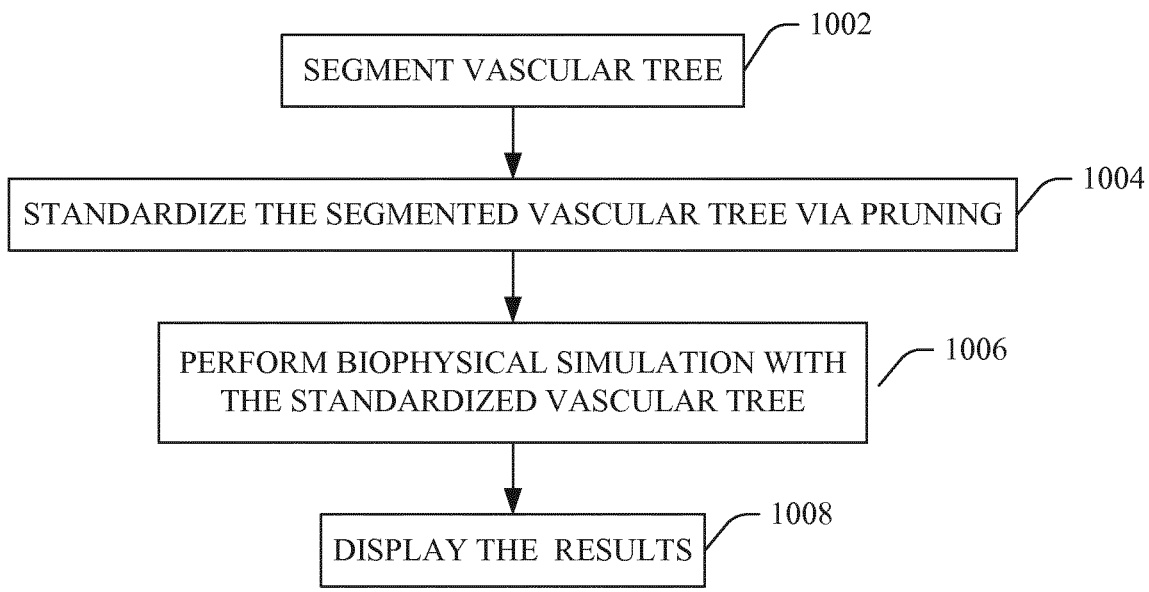
FIG. 10 illustrates an example method for determining a standardized vascular tree and an FFR index therefore.

FIG. 10 illustrates an example method. It is to be appreciated that the ordering of the above acts is not limiting. As such, other orderings are contemplated herein. In addition, one or more acts may be omitted and/or one or more additional acts may be included.

At 1002, a vascular tree is segmented from the volumetric image data (e.g., CT).

At 1004, the segmented vascular tree is standardized, as described herein and/or otherwise. For example, the segmented vascular tree can be standardized based on a predetermined set of pruning rules, such as those described in connection with FIG. 2, which prune off certain portions of certain vessels of the segmented vascular tree.

At 1006, a biophysical simulation is performed for the standardized segmented vascular tree.

At 1008, the results (e.g., the standardized segmented vascular tree and FFR index) are visually displayed via a display monitor.

Figure 11:
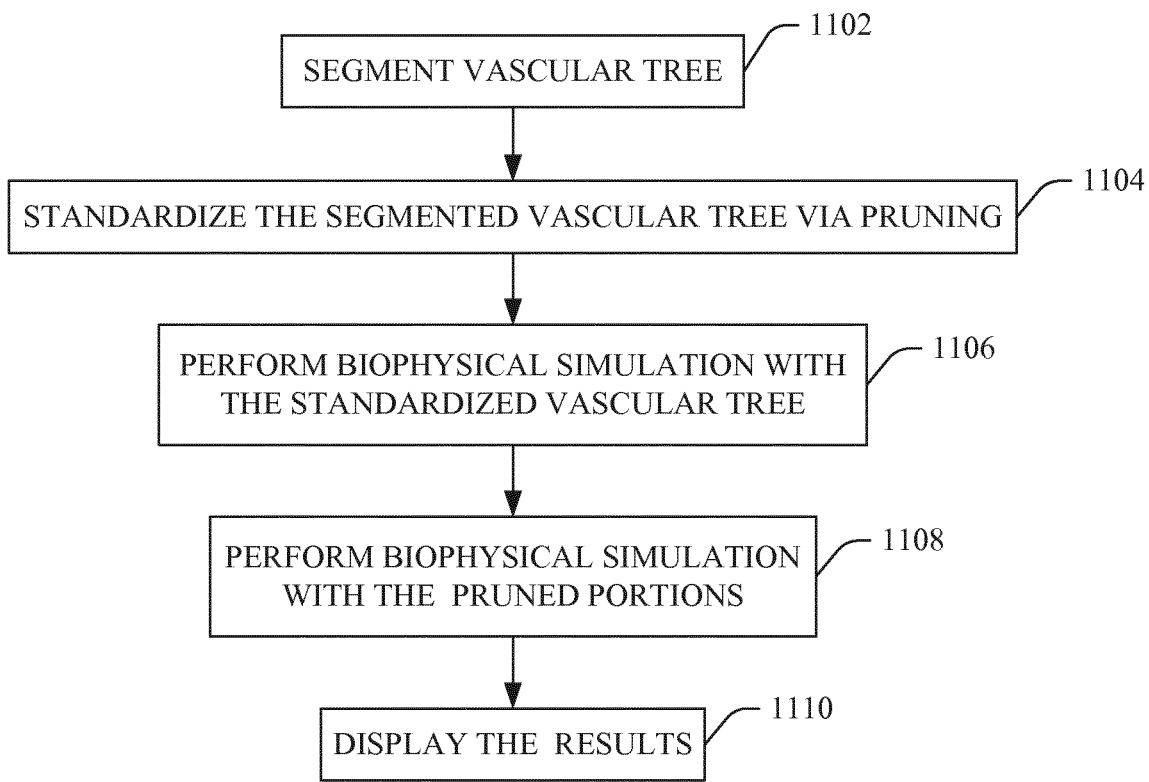
FIG. 11 illustrates an example method for determining a standardized vascular tree and an FFR index therefore and for portions thereof pruned off.

FIG. 11 illustrates another example method. It is to be appreciated that the ordering of the above acts is not limiting. As such, other orderings are contemplated herein. In addition, one or more acts may be omitted and/or one or more additional acts may be included.

At 1102, a vascular tree is segmented from the volumetric image data (e.g., CT).

At 1104, the segmented vascular tree is standardized, as described herein and/or otherwise. For example, the segmented vascular tree can be standardized based on a predetermined set of pruning rules, such as those described in connection with FIG. 2, which prune off certain portions of certain vessels of the segmented vascular tree.

At 1106, a biophysical simulation is performed for the standardized segmented vascular tree.

At 1108, a biophysical simulation is performed for the pruned portions, as described herein and/or otherwise.

At 1008, the results (e.g., the segmented vascular tree and FFR index for the standardized and pruned portions) are visually displayed via a display monitor.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium, which is not computer readable storage medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A computing system, comprising:
    a computer readable storage medium with computer executable instructions, including:
        a segmentation standardizer configured to determine, based on a predetermined set of pruning rules, a standardized vascular tree from a segmented vascular tree of volumetric image data; and
        a biophysical simulator configured to perform a biophysical simulation based on the standardized vascular tree;
    a processor configured to execute the segmentation standardizer to determine the standardized vascular tree, and configured to execute the biophysical simulator to perform a biophysical simulation based on the standardized vascular tree; and
    a display configured to display at least one of the standardized vascular tree and a result of the biophysical simulation.

2. The computing system of claim 1, wherein the predetermined set of pruning rules includes at least one of a main vessel pruning rule, a short vessel pruning rule, a location of interest pruning rule, a distal segment pruning rule, and a vessel diameter pruning rule.

3. The computing system of claim 2, wherein the processor, based on the main vessel pruning rule, prunes a main vessel only if a length of the main vessel, from an aorta to an end of the vessel, is greater than a predetermined main vessel length, and only up to the predetermined main vessel length.

4. The computing system of claim 3, wherein the processor, based on the short vessel pruning rule, prunes off a vessel only if a length of the short vessel is less than a predetermined short vessel length.

5. The computing system of claim 4, wherein the processor, based on the location of interest pruning rule, prunes an end of a vessel from a location of interest only if a length of the end from the location of interest is greater than a predetermined location of interest length and only up to the predetermined location of interest length.

6. The computing system of claim 5, wherein the processor, based on the distal segment pruning rule, prunes a distal end of a vessel from a branch only if a length of the distal end from the branch is greater than a predetermined distal segment length and only up to the predetermined distal segment length.

7. The computing system of claim 6, wherein the distal segment pruning rule is constrained by the main vessel pruning rule and the location of interest pruning rule.

8. The computing system of claim 6, wherein the processor, based on the vessel diameter pruning rule, prunes a vessel from an outlet of the vessel towards an inlet of the vessel up only if a vessel diameter of the vessel is greater than a predetermined vessel diameter and only until the predetermined vessel diameter is reached.

9. The computing system of claim 2, wherein the biophysical simulator further includes a pruned vascular segment processor configured to perform a biophysical simulation for only pruned portions of the segmented vascular tree.

10. The computing system of claim 9, wherein for a pruned portion that is a continuation of a pruned vessel, the processor utilizes a volumetric flow rate and an absolute pressure from the biophysical simulation of the standardized vascular tree as initial values for a simulation for just the pruned portion to determine the biophysical simulation for the pruned portion.

11. The computing system of claim 9, wherein for an entire pruned subtree, the processor simulates an entire hydraulic network by solving a system of nonlinear equations to obtain flows and pressures and to determine the biophysical simulation for the pruned subtree.

12. The computing system of claim 9, wherein for an entire pruned vessel or subtree pruned from another vessel, the processor determines a constant pressure and assigns constant values along the entire pruned vessel or subtree.

13. The computing system of claim 9, wherein the display is configured to display the segmented vascular tree and the simulation results for the standardized vascular tree and the pruned portions.

14. A non-transitory computer readable storage medium encoded with computer readable instructions, which, when executed by a processor of a computing system, causes the processor to:
execute a segmentation standardizer configured to determine, based on a predetermined set of pruning rules, a standardized vascular tree from a segmented vascular tree of volumetric image data;
execute a biophysical simulator configured to perform a biophysical simulation based on the standardized vascular tree; and
display via a display monitor configured to display at least one of the standardized vascular tree and a result of the biophysical simulation.

15. The computer readable storage medium of claim 14, wherein the predetermined set of pruning rules includes at least one of a main vessel pruning rule, a short vessel pruning rule, a location of interest pruning rule, a distal segment pruning rule, and a vessel diameter pruning rule.

16. The computing system of claim 15, wherein the predetermined set of pruning rules further includes a pruning rules based on a resolution of the volumetric image data.

17. The computing system of claim 15, wherein the predetermined set of pruning rules further includes a pruning rules based on at least one of a demographic of a subject of the volumetric image data and an anatomical characteristic of anatomy represented in the volumetric image data.

18. The computer readable storage medium of claim 14, wherein the predetermined set of pruning rules includes a main vessel pruning rule that causes the processor to prune a main vessel to a length of ten centimeters.

19. The computer readable storage medium of claim 14, wherein the predetermined set of pruning rules includes a short vessel pruning rule that causes the processor to remove a short vessel having a length of one centimeter or less.

20. The computer readable storage medium of claim 14, wherein the predetermined set of pruning rules includes a location of interest pruning rule that causes the processor to prune an end of a vessel from a location of interest until the end of the vessel is two centimeters from the location of interest.

21. The computer readable storage medium of claim 14, wherein the predetermined set of pruning rules includes a distal segment pruning rule that causes the processor to prune a distal end of a vessel from a branch until the distal end of the vessel is two centimeters from the branch.

22. The computer readable storage medium of claim 14, wherein the predetermined set of pruning rules includes a vessel diameter pruning rule that causes the processor to prune a vessel from an outlet of the vessel towards an inlet of the vessel until the diameter of the vessel is one and a half millimeters.

23. The computer readable storage medium of claim 14, wherein the processor is further configured to perform a biophysical simulation for only pruned portions of the segmented vascular tree.

24. A method, comprising:
standardizing a segmented vascular tree using a predetermined set of pruning rules to create a standardized vascular tree;
performing a biophysical simulation for the standardized vascular tree; and
displaying the standardized vascular tree and a result of the biophysical simulation.

25. The method of claim 24, wherein performing the biophysical simulation includes performing a computational fluid dynamic simulation for the standardized vascular tree.

26. The method of claim 24, further comprising:
performing a biophysical simulation for pruned portions of the segmented vascular tree based on the biophysical simulation for the standardized vascular tree to determine boundary conditions; and
displaying results of the biophysical simulation for the standardized vascular tree and the pruned portions.

27. The method of claim 26, wherein performing a biophysical simulation for the pruned portions includes performing a computational fluid dynamic simulation for the pruned portions.

* * * * *